US008748181B2

(12) United States Patent
Kuo et al.

(10) Patent No.: US 8,748,181 B2
(45) Date of Patent: *Jun. 10, 2014

(54) METHODS OF GENERATING PATTERNED SOFT SUBSTRATES AND USES THEREOF

(75) Inventors: Po-Ling Kuo, Cambridge, MA (US); Adam W. Feinberg, Cambridge, MA (US); Kevin Kit Parker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 541 days.

This patent is subject to a terminal disclaimer.

(21) Appl. No.: 12/994,187

(22) PCT Filed: May 22, 2009

(86) PCT No.: PCT/US2009/045001
§ 371 (c)(1),
(2), (4) Date: Mar. 17, 2011

(87) PCT Pub. No.: WO2010/011407
PCT Pub. Date: Jan. 28, 2010

(65) Prior Publication Data
US 2011/0189719 A1    Aug. 4, 2011

Related U.S. Application Data

(60) Provisional application No. 61/128,727, filed on May 23, 2008.

(51) Int. Cl.
*A61K 35/34* (2006.01)
*C12N 5/07* (2010.01)
*C12N 5/00* (2006.01)

(52) U.S. Cl.
USPC ............ 435/395; 435/325; 435/326; 435/375

(58) Field of Classification Search
None
See application file for complete search history.

(56) References Cited

U.S. PATENT DOCUMENTS

| 6,713,772 B2 | 3/2004 | Goodman et al. |
| 6,821,107 B1 | 11/2004 | Hara et al. |
| 6,829,035 B2 | 12/2004 | Yogev |
| 7,115,377 B2 | 10/2006 | Yao et al. |

(Continued)

FOREIGN PATENT DOCUMENTS

| EP | 0387975 | 9/1990 |
| EP | 1302535 | 4/2003 |

(Continued)

OTHER PUBLICATIONS

Lääniläinen, Eeva "Soft Lithography for Surface Micropatterning", Thesis, Helsinki Univ. of Tech., Jun. 29, 2006, 94 pp.*

(Continued)

*Primary Examiner* — Chris R Tate
*Assistant Examiner* — Aaron J Kosar
(74) *Attorney, Agent, or Firm* — McCarter & English, LLP; Maria Laccotripe Zacharakis; Debra L. Nagle

(57) ABSTRACT

The present invention provides methods of generating and devices of patterned soft substrates, on which cells may be seeded, as well as methods of using these substrates. Devices containing these patterned soft substrates are also provided.

16 Claims, 3 Drawing Sheets

(56) References Cited

U.S. PATENT DOCUMENTS

| | | |
|---|---|---|
| 7,122,307 B2 | 10/2006 | Rosen et al. |
| 2001/0023073 A1 | 9/2001 | Bhatia et al. |
| 2003/0059537 A1 | 3/2003 | Chilkoti et al. |
| 2003/0134331 A1 | 7/2003 | Marks et al. |
| 2004/0009566 A1 | 1/2004 | Okano et al. |
| 2004/0048239 A1 | 3/2004 | Farinas et al. |
| 2004/0078090 A1 | 4/2004 | Binette et al. |
| 2004/0101819 A1 | 5/2004 | Montemagno et al. |
| 2005/0048414 A1* | 3/2005 | Harnack et al. ............... 430/322 |
| 2005/0080402 A1 | 4/2005 | Santamore et al. |
| 2005/0085847 A1 | 4/2005 | Galdonik et al. |
| 2005/0202569 A1 | 9/2005 | Sakaino et al. |
| 2006/0003439 A1 | 1/2006 | Ismagilov et al. |
| 2006/0029922 A1 | 2/2006 | Van Eelen et al. |
| 2006/0071286 A1 | 4/2006 | Axelrod et al. |
| 2006/0134692 A1 | 6/2006 | Emmert-Buck et al. |
| 2006/0136182 A1 | 6/2006 | Vacanti et al. |
| 2006/0153816 A1 | 7/2006 | Brown et al. |
| 2007/0053996 A1 | 3/2007 | Boyden et al. |
| 2007/0190646 A1 | 8/2007 | Engler et al. |
| 2008/0118985 A1 | 5/2008 | Torres et al. |
| 2009/0023773 A1 | 1/2009 | Vohra et al. |
| 2009/0317852 A1 | 12/2009 | Parker et al. |
| 2010/0196432 A1 | 8/2010 | Feinberg et al. |
| 2010/0330644 A1 | 12/2010 | Feinberg et al. |
| 2011/0189719 A1 | 8/2011 | Kuo et al. |
| 2012/0029416 A1 | 2/2012 | Parker et al. |
| 2012/0142556 A1 | 6/2012 | Parker et al. |
| 2013/0046134 A1 | 2/2013 | Parker et al. |

FOREIGN PATENT DOCUMENTS

| | | |
|---|---|---|
| WO | WO 2004/014212 | 2/2004 |
| WO | WO 2006/068972 | 6/2006 |
| WO | WO2010/127280 | 11/2010 |
| WO | WO 2011102991 | 8/2011 |
| WO | WO 2012006320 | 1/2012 |
| WO | WO 2012048242 | 4/2012 |

OTHER PUBLICATIONS

Narasimhan, SV; Goodwin, RL; Borg, TK; Dawson, DM; Gao, BZ "Multiple Beam Laser Cell Micropatterning System" Optical Trapping and Optical Micromanipulation, Proc. SPIE., Oct. 18, 2004, 5514, pp. 437-445.*

McDonald, JC and Whitesides, GM "Poly(dimethylsiloxane) as a Material for Fabricating Microfluidic Devices" Acc. Chem. Res., Jul. 2002, 35(7), pp. 491-499.*

Alford et al., "Biohybrid Thin Films for Measuring Contractility in Engineered Cardiovascular Muscle." Biomaterials. 2010, 31: 3613-3621.

Bol et al., "Computational modeling of muscular thin films for cardiac repair." Computational Mechanics. Sep. 13, 2008;43(4):535-44.

Bray et al., "Sarcomere alignment is regulated by myocyte shape." Cell Motil Cytoskeleton. Aug. 2008;65(8):641-51.

Bursac et al., "Cardiomyocyte cultures with controlled macroscopic anisotropy: a model for functional electrophysiological studies of cardiac muscle." Circ Res. Dec. 13, 2002;91(12):e45-54.

Feinberg et al., "Muscular thin films for building actuators and powering devices." Science. Sep. 7, 2007;317(5843):1366-1370.

Geisse et al., "Micropatterning Approaches for Cardiac Biology." In: Khademhosseini A, Toner M, Borenstein JT, Takayama S, editors. Micro- and Nanoengineering of the Cell Microenvironment: Technologies and Applications. Boston: Artech House; 2008, p. 341-357.

Lehnert et al., "Cell behavior on micropatterned substrata: limits of extracellular matrix geometry for spreading and adhesion." Journal of Cell Science, 2004, vol. 117, pp. 41-52.

Tan et al., "Simple Approach to Micropattern Cells on Common Culture Substrates by Tuning Substrate Wettability", Tissue Eng., 2004, 10:865-72.

Park et al., "Real-time measurement of 17,18 the contractile forces of self-organized cardiomyocytes on hybrid biopolymer microcantilevers", Analytical Chemistry, American Chemical Society, US,vo 1. 77, No. 20, Oct. 15, 2005.

Parker et al., "Myofibrillar architecture in engineered cardiac myocytes." Circ Res. Aug. 15, 2008;103(4):340-2.

Parker et al., "Ectracellular matrix, mechanotransduction and struction hierarchies in heart tissue engineering." Phil Trans R. Soc B, Epub Jun. 22, 2007, vol. 362, pp. 1267-1279.

Pelham et al., "Cell locomotion and focal adhesions are regulated by substrate flexibility" (Proc. Natl. Acad. Sci. USA, 1997, 94: 13661-13665).

Wang et al., "Micropatterning Tractional Forces in Living Cells", Cell Motil. Cytoskeleton, 2002, 52:97-106.

Yang et al., "Fabrication of well-defined PLGA scaffolds using novel microembossing and carbon dioxide bonding", Biomaterials, 2005, vol. 26, pp. 2585-2594.

Xi et al., "Development of a Self-Assembled Muscle-Powered Piezoelectric Microgenerator", NSTI-Nanotech, 2004, vol. 1, pp. 3-6.

* cited by examiner

METHODS OF GENERATING PATTERNED SOFT SUBSTRATES AND USES THEREOF

RELATED APPLICATIONS

This application is a 35 U.S.C. §371 national stage filing of International Application No. PCT/US2009/45001, filed on May 22, 2009, which claims priority to U.S. Provisional Application No. 61/128,727, filed on May 23, 2008, the entire contents of which are incorporated herein by this reference.

GOVERNMENT SUPPORT

The invention was supported, in whole or in part, by grant Prime Award Number FA9550-01-1-0015 from the Defense Advanced Research Projects Agency (DARPA) under the United States Department of Defense. The United States Government has certain rights in the invention.

BACKGROUND OF THE INVENTION

The understanding of cellular functions relating to, for example, proliferation, migration, division, or differentiation requires an understanding of the mechanics of a cell's underlying cytoskeletal architecture. The architecture of the cytoskeleton is related to the cell's shape, which can be dictated by a cell's surrounding environment. Therefore, the cytoskeleton is in large part determined by a cell's responses to environmental stimuli.

Although various techniques have been developed to reproduce a cell's in vivo microenvironment, in general, it has not been possible to reproduce all of these aspects of a cell's in-vivo microenvironment within an in-vitro culture.

For example, Bhatia et al. (U.S. Patent Publication No. 2001/0023073) describe a hard, i.e., glass, substrate differentially functionalized through the aid of defined patterns developed using photoresist. Tan et al. (*Tissue Eng.*, 2004, 10:865-72) describe differentially functionalized polydimethylsiloxane (PDMS) substrates. However, these substrates are hard substrates and uncharacteristic of living tissue.

Pelham and Wang (*Proc. Natl. Acad. Sci. USA*, 1997, 94: 13661-13665) describe a method of producing polyacrylamide cell substrates. However, these substrates are completely covered by a functionalizing linker molecule and, thus, do not replicate the cell's surrounding environment in vivo. Wang et al. (*Cell Motil. Cytoskeleton*, 2002, 52:97-106) describe a differentially functionalized polyacrylamide substrate developed using a first mask to deposit photoresist and subsequently producing a second mask of polymer (polydimethylsiloxane (PDMS)) to create a pattern on the substrate. Thus, this technique requires the production of multiple masks, and because the PDMS membranes must be sufficiently thick to be handled, and the channels sufficiently high to allow reasonable flow rates to functionalize the substrate, the spatial resolution, as well as the complexity, types and sizes of patterns are limited. Furthermore, since these polymer membranes are very thin, they are easily distorted, limiting the ability to precisely generate long, large patterns that are separated by spacing smaller than the length scale of the pattern.

Therefore, there exists a need in the art for methods for producing soft substrates that are tunable to mimic physiological tissues, that are differentially functionalized, and can be easily produced. In addition, such methods must allow for high fidelity pattern transfer and enhanced reproducibility.

SUMMARY OF THE INVENTION

The present invention allows for the generation of patterned soft substrates with microscale and nanoscale control. The methods described herein are simpler than methods previously described, yield membrane/mask(s) that are stiff enough to allow them to be easily manipulated yet remain flexible, have high fidelity of pattern transfer, and enhanced reproducibility.

The soft substrate may be patterned with any desired shape, e.g., a geometric shape, such as a square, circle, triangle, line, and combinations thereof. The soft substrate itself is typically flat such that the mask can make conformal contact. However, the substrate may be curved. In the latter case, the mask replicates those curves in order to still make conformal contact.

Accordingly, in one aspect the present invention provides methods for generating a patterned soft substrate. The methods include, providing a base layer; depositing a sacrificial polymer on the base layer, thereby generating a sacrificial polymer layer; depositing a photoresist onto the sacrificial polymer layer, thereby generating a photoresist layer; placing a mask on top of the photoresist layer and exposing the photoresist layer to electromagnetic radiation, thereby generating a patterned photoresist complementary mask; releasing the patterned photoresist complementary mask from the sacrificial polymer layer; placing the patterned photoresist complementary mask onto a soft substrate; and functionalizing the soft substrate by contacting the soft substrate with a linker molecule and a biopolymer; thereby generating a patterned soft substrate. In some embodiments, the patterned photoresist complementary mask is removed prior to functionalization. In other embodiments, the patterned photoresist complementary mask is not removed prior to functionalization.

The methods of the invention may further comprise seeding cells, e.g., myocytes, on the patterned soft substrate.

The base layer may be a silicon wafer, a glass cover slip, a multi-well plate or tissue culture plate.

In certain embodiments of the methods of the invention the sacrificial polymer is deposited on the base layer via spin coating and/or the photoresist is deposited on the sacrificial polymer layer via spin coating.

The sacrificial polymer may be non-cross-linked poly(N-Isoproylacrylamide) in which case the patterned photoresist complementary mask is released from the sacrificial polymer layer by dropping the temperature to 35° C. or less; crosslinked N-Isopropylacrylamide in which case the patterned photoresist complementary mask is released from the sacrificial polymer layer by dropping the temperature to 35° C. or less; an electrically actuated polymer in which case the patterned photoresist complementary mask is released from the sacrificial polymer layer by applying an electric potential to the sacrificial polymer layer; or a degradable biopolymer in which case the patterned photoresist complementary mask is released from the sacrificial polymer layer by dissolving the sacrificial polymer layer.

The biopolymer can be a protein, e.g., fibronectin, a carbohydrate, a lipid, a nucleic acid, or combinations thereof, such as a glycoprotein, a glycolipid, or a proteolipid.

In one embodiment, linker molecule is a bifunctional or multifunctional linker molecule, for example, the linker molecule can be N-Sulfosuccinimidyl 6-hexanoate (SANPAH).

In one embodiment, the soft substrate has a Young's modulus of about 1 to about 100,000 pascal (Pa), e.g., the soft substrate is a polyacrylamide gel.

In one embodiment, the photoresist is an epoxy-novolac resin, e.g., 1-Methoxy-2-propanol acetate (SU-8).

In another aspect, the invention provides patterned soft substrates prepared according to the methods of the invention, such as cellular arrays.

In yet another aspect, the invention provides methods for assaying a cellular activity. The methods include providing a patterned soft substrate seeded with cells; and evaluating a cellular activity, e.g., the contractility of a cell, the mechano-electrical coupling of a cell, the mechano-chemical coupling of a cell, and/or the response of a cell to varying degrees of substrate rigidity, of the cells seeded on said patterned soft substrate, e.g., using traction force microscopy, thereby assaying a cellular activity.

In another aspect, the invention provides methods for identifying a compound that modulates a cellular activity. The methods include contacting the patterned soft substrate seeded with cells with a test compound; and determining the effect of the test compound on a cellular activity of the cells seeded on said patterned soft substrate in the presence and absence of the test compound, wherein a modulation of the cellular activity in the presence of said test compound as compared to the cellular activity in the absence of said test compound indicates that said test compound modulates a cellular activity, thereby identifying a compound that modulates a cellular activity.

In yet another aspect, the invention provides methods for identifying a compound useful for treating or preventing a disease. The methods include contacting the patterned soft substrate seeded with cells with a test compound; and determining the effect of the test compound on a cellular activity of the cells seeded on said patterned soft substrate in the presence and absence of the test compound, wherein a modulation of cellular activity in the presence of said test compound as compared to the cellular activity in the absence of said test compound indicates that said test compound modulates a cellular activity, thereby identifying a compound useful for treating or preventing a disease.

The cellular activity may be a biomechanical activity, e.g., contractility, cell stress, cell swelling, and rigidity, or an electrophysiological activity, e.g., a voltage parameter selected from the group consisting of action potential, action potential duration (APD), conduction velocity (CV), refractory period, wavelength, restitution, bradycardia, tachycardia, and reentrant arrhythmia; a calcium flux parameter selected from the group consisting of intracellular calcium transient, transient amplitude, rise time (contraction), decay time (relaxation), total area under the transient (force), restitution, focal and spontaneous calcium release.

In another embodiment, the methods further comprise applying a stimulus to the cells seeded on the patterned soft substrate.

In yet another embodiment, the patterned soft substrate is cultured in the presence of a fluorophor, e.g., a voltage-sensitive dye, e.g., an electrochromic dye, e.g., a styryl dye and a merocyanine dye, or a dye comprising RH-421 or di-4-ANEPPS; or an ion-sensitive dye, e.g., a calcium sensitive dye, e.g., X-Rhod, aequorin, Fluo3, Fluo5, and Rhod2.

In one embodiment, the fluorophore is a dye pair selected from the group consisting of di-2-ANEPEQ and calcium green; di-4-ANEPPS and Indo-1; di-4-ANEPPS and Fluo-4; RH237 and Rhod2; and, RH-237 and Fluo-3/4.

The patterned soft substrate may be seeded with cardiomyocytes; vascular smooth muscle cells; smooth muscle cells or striated muscle cells.

DETAILED DESCRIPTION OF THE INVENTION

Described herein are improved methods for generating patterned (nanopatterned and micropatterned) soft substrates on which cells may be seeded. For example, the soft substrates described herein may be patterned with a desired shape having a dimension of about 10 nanometers to about 1,000 nanometers, about 10 nanometers to about 500 nanometers, about 10 nanometers to about 100 nanometers, about 50 nanometers to about 1,000 nanometers, about 50 nanometers to about 500 nanometers, about 50 nanometers to about 100 nanometers, or about 500 nanometers to about 1,000 nanometers. The soft substrates produced according to the methods of the invention may, for example, be used to study and/or to measure the contractility of cells with engineered shapes and connections, the mechano-electrical coupling of cells, the mechano-chemical coupling of cells, and/or the response of the cells to varying degrees of substrate rigidity. The soft substrates are also useful for investigating tissue developmental biology and disease pathology, as well as in drug discovery and toxicity testing.

I. Methods for Production of the Patterned Soft Substrates of the Invention

Figure 3:
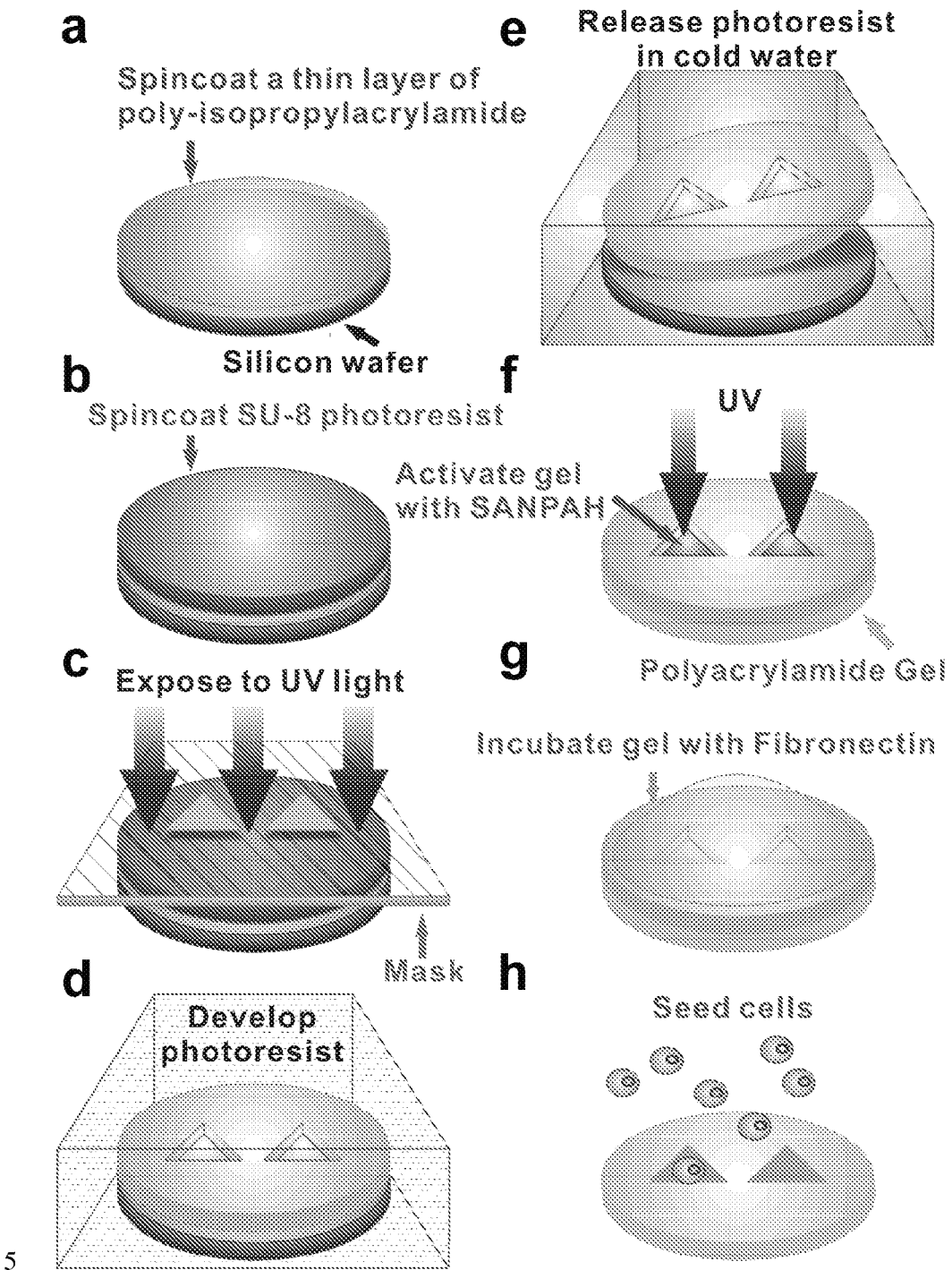
FIG. 3 depicts a schematic representation of one embodiment of the invention. After a thin layer of poly-N-iso-propylacrylamide (PIPAAM) was spin-coated on a silicon wafer (a), 1-Methoxy-2-propanol acetate (SU-8) photoresist was spin-coated on top of the PIPAAM (b), treated with UV light through a photolithographic mask (c), and developed to obtain a complementary master (d). The master was immersed in ice water to release the photoresist membrane (e). The photoresist membrane was placed on the surface of polyacrylamide gels and sulfo-SANPAH was added to the gel surface, photoactivated by UV light (f). FN solution was then added to react with the photoactivated gel (g). After removal of the photoresist membrane, the gel was immediately used for cell plating (h).

In one aspect, the present invention provides methods for preparing a patterned soft substrate. The methods include providing a base layer; depositing a sacrificial polymer on the base layer, thereby generating a sacrificial polymer layer; depositing a photoresist onto the sacrificial polymer layer, thereby generating a photoresist layer; placing a mask on top of the photoresist layer and exposing the photoresist layer to electromagnetic radiation, thereby generating a patterned photoresist complementary mask; releasing the patterned photoresist complementary mask from the sacrificial polymer layer; placing the patterned photoresist complementary mask onto a soft substrate; and functionalizing the soft substrate by contacting the soft substrate with a linker molecule and a biopolymer; thereby generating a patterned soft substrate. One embodiment of the methods of the invention is depicted in FIG. 3.

The base layer used in the methods of the invention is formed of a rigid or semi-rigid material, such as a plastic, metal, ceramic, or a combination thereof. In particular embodiments, the Young's modulus of the base material used to form the base layer is greater than 1 mega-pascal (MPa). The base layer material may also be transparent, so as to facilitate observation. Examples of suitable base layer material include polymethylmethacrylate, polystyrene, polyethylene terephthalate film, silicon wafer, or gold. In one embodiment, the base layer is a silicon wafer, a glass cover slip, a multi-well plate or tissue culture plate.

The sacrificial polymer layer may be applied to the rigid base layer by "depositing" the sacrificial polymer onto the base layer. Depositing refers to a process of placing or applying an item or substance onto another item or substance (which may be identical to, similar to, or dissimilar to the first item or substance). Depositing may include, but is not limited to, methods of using spraying, dip casting, spin coating, or other methods to associate the items or substances. The term depositing includes applying the item or substance to substantially the entire surface as well as applying the item or substance to a portion of the surface.

In one embodiment, spin coating is used to deposit the sacrificial polymer layer to the base material. "Spin coating", as used herein, refers to a process wherein the base layer is mounted to a chuck under vacuum and is rotated to spin the base layer about its axis of symmetry and a liquid or semi-liquid substance, e.g. a polymer, is dripped onto the base layer, with the centrifugal force generated by the spin causing the liquid or semi-liquid substance to spread substantially evenly across the surface of the base layer. The resulting sacrificial polymer layer serves to temporarily secure additional coatings that are subsequently formed thereon.

In one embodiment, the sacrificial polymer is a thermally sensitive polymer that is melted or dissolved to cause the release of the patterned photoresist complementary mask. An example of such a polymer is linear, non-cross-linked poly(N-Isopropylacrylamide), which is a solid when dehydrated, and which is a solid at about 37° C. (wherein the polymer is hydrated but relatively hydrophobic). However, when the temperature is dropped to about 35° C. to about 32° C. or less (where the polymer is hydrated but relatively hydrophilic), the polymer becomes a liquid, thereby releasing the patterned photoresist complementary mask (Feinberg et al. (2007) Science 317:1366-1370).

In another embodiment, the sacrificial polymer becomes hydrophilic, thereby releasing hydrophobic coatings, with a change in temperature. For example, the sacrificial polymer can be hydrated, crosslinked N-Isopropylacrylamide, which is hydrophobic at about 37° C. and hydrophilic at about 35° C. or less (e.g., about 35° C. to about 32° C.).

In yet another embodiment, the sacrificial polymer is an electrically actuated polymer that becomes hydrophilic upon application of an electric potential to thereby release a hydrophobic structure coated thereon. Examples of such a polymer include poly(pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s.

In still another embodiment, the sacrificial polymer is a degradable biopolymer that can be dissolved to release a structure coated thereon. In one example, the polymer (e.g., polylactic acid, polyglycolic acid, poly(lactic-glycolic) acid copolymers, or nylons) undergoes time-dependent degradation by hydrolysis. In another example, the polymer undergoes time-dependent degradation by enzymatic action (e.g., fibrin degradation by plasmin, collagen degradation by collagenase, or fibronectin degradation by matrix metalloproteinase).

In yet still another embodiment, the sacrificial polymer is an ultra-hydrophobic polymer with a surface energy lower than the photoresist adhered to it. In this case, mild mechanical agitation will "pop" the patterned photoresist complementary mask off. Examples of such a polymer include but are not limited to alkylsilanes (octadecyltrichlorosilane and isobutyltrimethoxysilane), fluoroalkylsilanes (tridecafluorotetrahydrooctyltrichlorosilane, trifluoropropyltrichlorosilane and heptadecafluorotetrahydrodecyltrichlorosilane), silicones (methylhydrosiloxane-dimethylsiloxane copolymer, hydride terminated polydimethylsiloxane, trimethylsiloxy terminated polydimethylsiloxane and diacetoxymethyl terminated polydimethylsiloxane), fluorinated polymers (polytetrafluoroethylene, perfluoroalkoxy and fluorinated ethylene propylene).

The sacrificial polymer layer provides temporary adhesion of the base layer to a photoresist layer. A photoresist layer may be applied to the sacrificial polymer layer by depositing a photoresist onto the sacrificial polymer layer. In one embodiment, spin coating (as described above with reference to applying the sacrificial polymer layer to the base layer) is used to apply a photoresist to the sacrificial polymer layer. "Photoresist" is any substance that is sensitive to electromagnetic radiation, e.g., wavelengths of light in the ultraviolet or shorter spectrum (<400 nm). A photoresist may be positive or negative.

A "positive photoresist" is a type of photoresist in which the portion of the photoresist that is exposed to light becomes soluble to the photoresist developer and the portion of the photoresist that is unexposed remains insoluble to the photoresist developer.

A "negative photoresist" is a type of photoresist in which the portion of the photoresist that is exposed to light becomes essentially insoluble to the photoresist developer. The unexposed portion of the photoresist is solubilized by the photoresist developer.

Non-limiting examples of photoresist materials include 1-Methoxy-2-propanol acetate (SU-8), bisazides, poly(vinyl cinnamate), and novolaks, polymethylmethacrylates (PMMA), epoxies.

In order to prepare a patterned photoresist complementary mask comprising the photoresist and the sacrificial polymer layer, a mask (comprising a desired shape), e.g., a solid mask, such as a photolithographic mask, is provided and placed on top of the photoresist layer. Subsequently, a portion of the photoresist layer (i.e., the portion of the photoresist not covered by the solid mask) is exposed to electromagnetic radiation. A suitable shape may be any desired shape, such as a geometric shape, e.g., a circle, square, rectangle, triangle, line, or combinations thereof. In other embodiments, the shape may be the shape of an organ, or portion thereof.

The mask, e.g., a micropatterned mask and/or a nanopatterned mask, placed on top of the photoresist layer is typically fabricated by standard photolithographic procedure, e.g., by means of electron beam lithography. Other methods for creating such masks include focused energy for ablation (micromachining) including lasers, electron beams and focused ion beams. Similarly, chemical etchants may be used to erode materials through the photoresist when using an alternative mask material. Examples of chemical etchants include hydrofluoric acid and hydrochloric acid. Colloidal lithography may also be used to generate a nanomachined mask.

Any suitable material, e.g., a material that has a flat surface, e.g., a metal (gold, silver, platinum, or aluminum), a ceramic (alumina, titanium oxide, silica, or silicon nitride), may be used for making the mask.

In order to release the sacrificial polymer layer from the patterned photoresist complementary mask, the sacrificial polymer layer is exposed to conditions that dissolve or allow the sacrificial polymer layer to switch states.

For example, a sacrificial polymer layer formed of poly-N-iso-propylacrylamide (PIPAAM) (non-cross-linked) will dissolve in an aqueous media at a temperature less than about 35° C. or less than about 32° C. (e.g., about 35° C. to about 32° C.). In another example, a sacrificial polymer layer is formed of PIPAAM (cross-linked) will switch from a hydrophobic to hydrophilic state in an aqueous media at a temperature less than 35° C. or less than about 32° C. (e.g., about 35° C. to about 32° C.). The hydrophilic state will release the sacrificial polymer layer from the patterned photoresist complementary mask. In yet another embodiment, the sacrificial polymer layer includes a conducting polymer, such as polypyrrole, that can be switched from a hydrophobic to hydrophilic state by applying a positive bias that switches the conducting polymer from a reduced to an oxidized state. In additional embodiments, the sacrificial polymer layer can include a degradable polymer and/or polymer that undergoes time-dependent degradation by hydrolysis (as is the case, for example, for polylactic and polyglycolic acid) or by enzymatic action (for example, fibrin degradation by plasmin).

Once the patterned photoresist complementary mask is released from the sacrificial polymer layer, it is placed onto a soft substrate. A "soft substrate" is any material that is flexible, pliable, or malleable when exposed to an external force. Other physical characteristics common to soft substrates suitable for use in the methods of the invention include linear elasticity and incompressibility. Generally, soft substrates have a Young's modulus in the range of about 1 to about 100,000 pascal (Pa). The soft substrates of the present invention include those that may be tunable to the stiffness of physiological tissues with a Young's modulus of about 1,000 to about 100,000 Pa, about 1,000 to about 5,000 Pa, about 1,000 to about 10,000 Pa, about 5,000 to 10,000 Pa, about 5,000 to about 20,000 Pa, about 10,000 to about 20,000 Pa, about 10,000 to about 50,000 Pa, about 20,000 to about 50,000 Pa, about 30,000 to about 50,000 Pa, about 40,000 to about 50,000 Pa, about 50,000 to about 100,000 Pa, about 60,000 to about 100,000 Pa, about 70,000 to about 100,000 Pa, about 80,000 to about 100,000 Pa, about 90,000 to about 100,000 Pa. In one embodiment, the soft substrate for use in the methods of the invention is prepared from a single material. In another embodiment, the soft substrate is prepared from more than one material. In yet other embodiments of the invention, a soft substrate for use in the methods of the invention is prepared by layering one or more soft substrates, e.g., to mimic tissue layers in vivo.

Non-limiting examples of soft substrates include polyacrylamide gels, poly(N-isopropylacrylamide), pHEMA, collagen, fibrin, gelatin, alginate, and dextran.

The soft substrate itself is typically flat such that the patterned photoresist complementary mask may make conformal contact. However, the substrate may be curved. In the latter case, the patterned photoresist complementary mask replicates those curves in order to still make conformal contact.

In one embodiment of the invention, the soft substrates for use in the methods of the invention are natural soft substrates. For example, physiological tissues having a Young's modulus in the range of about 1,000 Pa to about 30,000 Pa are natural soft substrates that may be used in the methods of the invention. These tissues include skin, muscle, and other visceral tissue, brain, spinal cord, peripheral nerve, adipose tissue, cartilage, other internal organs.

In another embodiment of the invention, the soft substrates for use in the methods of the invention are artificial soft substrates. Artificial soft substrates may be composed of polymers, such as polyacrylamide. Acrylamide may be polymerized into a gel with a finely-tuned stiffness. By varying the relative amounts of monomeric acrylamide and bis acrylamide, the stiffness of the resulting polyacrylamide gel may be increased (by using a higher relative amount of bis acrylamide) or decreased (by using a lower relative amount of acrylamide). Furthermore, the addition of additives such as polypyrrole and poly-ethyl-glycol will alter the stiffness of a polyacrylamide gel.

The soft substrate can be any acrylic acid-based hydrogel constructed by free radical polymerization, such as polyacrylamide, poly(N-isopropylacrylamide), and poly(2-hydroxyethyl methacrylate). The monomeric acrylamide may be cross-linked by any diacrylate group, such as ethylegeglycol dimethacrylate and 1,4-butanediol dimethacrylate, or by N,N' methylenebisacrylamide. The stiffness of the polymerized acrylamide may be tuned by varying the ratio of the cross-linker to the acrylamide subunit. In addition, the stiffness of the gel may be modified by co-polymerizing the acrylamide with other polymers, such as polypyrrole and polyethyleneglycol. The acrylamide may be co-polymerized with polyacetylene group such as polypyrrole and polyaniline to give rise to a conductive polymer.

The soft substrates may also be other soft, biocompatible gels. These include hydrogels composed of proteins such as gelatin, collagen, arginine, fibrin, and fibronectin, glucose molecules such as dextran, and glycoprotein such as hyaluronate.

In order to functionalize a soft substrate, a soft substrate is contacted with a functional linker molecule, e.g., a bifunctional or multifunctional linker molecule, and a biopolymer. The patterned photoresist complementary mask may be removed from the soft substrate prior to the addition of the biopolymer or may remain in place while the soft substrate is contacted with the biopolymer. In one embodiment, following contacting the soft substrate with a linker molecule, e.g., a bifunctional linker molecule, a second patterned photoresist complementary mask is placed in conformal contact with the linker molecule deposited soft substrate.

A "linker molecule", as used herein, is well-known in the art and refers to a first molecule that may associate with a second molecule to attach the second molecule to a third molecule, where the first, second, and third molecules may be identical, similar, or dissimilar to one another. These may include bifunctional linker molecules and multifunctional linker molecules. A bifunctional linker molecule has two linking moieties, e.g., two linking moieties that are activated using different methods. A multifunctional linker molecular has at least three linking moieties, e.g., where the three linking moieties include at least two linking moieties that are activated using different methods. Non-limiting examples of a functional linker molecules include N-Sulfosuccinimidyl 6-hexanoate (sulfo-SANPAH) or N-succinimidyl ester of acrylamidohexanoic acid.

A linker molecule may be activated prior to contacting the soft substrate with an appropriate biopolymer. "Activating", e.g., activating a linking molecule, refers to use of a method that allows a linking moiety of a linking molecule to associate with another molecule. Non-limiting examples of activating methods include ultraviolet radiation, chemical activation, thermal, or physical activation. For example, sulfo-SANPAH contains a nitrophenyl azide, which is activated by ultraviolet light, and a sulfo-N-hydroxysuccinimide ester, which is chemically activated by amino groups.

"Biopolymer" refers to any proteins, carbohydrates, lipids, nucleic acids or combinations thereof, such as glycoproteins, glycolipids, or proteolipids.

Examples of suitable biopolymers that may be used for substrate functionalization include, without limitation:

(a) extracellular matrix proteins to direct cell adhesion and function (e.g., collagen, fibronectin, laminin, vitronectin, or polypeptides (containing, for example the well known—RGD—amino acid sequence));

(b) growth factors to direct specific cell type development cell (e.g., nerve growth factor, bone morphogenic proteins, or vascular endothelial growth factor);

(c) lipids, fatty acids and steroids (e.g., glycerides, non-glycerides, saturated and unsaturated fatty acids, cholesterol, corticosteroids, or sex steroids);

(d) sugars and other biologically active carbohydrates (e.g., monosaccharides, oligosaccharides, sucrose, glucose, or glycogen);

(e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins (selectins, immunoglobulins, hormones such as human chorionic gonadotropin, Alpha fetoprotein or Erythropoietin (EPO)); proteolipids (e.g., N-myristoylated, palmitoylated and prenylated proteins); and glycolipids (e.g., glycoglycerolipids, glycosphingolipids, or glycophosphatidylinositols));

(f) biologically derived homopolymers, such as polylactic and polyglycolic acids and poly-L-lysine;

(g) nucleic acids (e.g., DNA or RNA);

(h) hormones (e.g., anabolic steroids, sex hormones, insulin, or angiotensin);

(i) enzymes (e.g., oxidoreductases, transferases, hydrolases, lyases, isomerases, ligases; examples: trypsin, collegenases, or matrix metalloproteinases);

(j) pharmaceuticals (e.g., beta blockers, vasodilators, vasoconstrictors, pain relievers, gene therapy, viral vectors, or anti-inflammatories);

(k) cell surface ligands and receptors (e.g., integrins, selectins, or cadherins); and (l) cytoskeletal filaments and/or motor proteins (e.g., intermediate filaments, microtubules, actin filaments, dynein, kinesin, or myosin).

Typically, a soft substrate will be contacted with a single linker molecule and a single biopolymer. However, a soft substrate may be contacted with two or more linker molecules and/or two or more biopolymers to create, e.g., a boundary condition, such as those described in PCT/US2008/011173, the contents of which are incorporated in their entirety by reference. For example, one linker molecule may be used to adhere a particular biopolymer to the soft substrate, e.g., a biopolymer with a particular cell type specificity, and a second linker molecule may be used to adhere a particular biopolymer with a different cell type specificity to the soft substrate. In practicing the invention, a variety of techniques can be used to foster selective cell adhesion of two or more cell types to the substrate. Included, without limitation, are methods such as localized protein adsorption, organosilane surface modification, alkane thiol self-assembled monolayer surface modification, wet and dry etching techniques for creating three-dimensional substrates, radiofrequency modification, and ion-implantation (Lom et al., 1993, J. Neurosci. Methods 50:385-397; Brittland et al., 1992, Biotechnology Progress 8:155-160; Singhvi et al., 1994, Science 264:696-698; Singhvi et al., 1994, Biotechnology and Bioengineering 43:764-771; Ranieri et al., 1994, Intl. J. Devel. Neurosci. 12 (8):725-735; Bellamkonda et al., 1994, Biotechnology and Bioengineering 43:543-554; and Valentini et al., 1993, J. Biomaterials Science Polymer Edition 5 (½):13-36).

In another embodiment, the soft substrates are functionalized by contacting the soft substrate with a repellent. As used herein, a "repellent" is a composition that, relative to the substrate to which it is applied, inhibits adhesion of a biopolymer and/or particular cell type, thereby causing a first particular cell type to adhere preferentially to the substrate. Agarose, hyaluronic acid, and alginate are examples of suitable repellents. In this embodiment, the patterned photoresist complementary mask is removed (or in the case of use of multiple patterned photoresist complementary masks, the first patterned photoresist complementary mask is removed and optionally a second patterned photoresist complementary mask is placed on the soft substrate) prior to, e.g., seeding cells.

Cells may be seeded onto the patterned soft substrates of the invention. Such cells may include, without limitation, nerve cells, muscle cells, or skin cells. Muscle cells include smooth muscle cells, striated muscle cells (skeletal), or cardiac cells. Stem cells including embryonic (primary and cell lines), fetal (primary and cell lines), adult (primary and cell lines) and iPS (induced pluripotent stem cells). Cells may be normal cells or abnormal cells (e.g., those derived from a diseased tissue, or those that are physically or genetically altered to achieve a abnormal or pathological phenotype or function), normal or diseased cells derived from embryonic stem cells or induced pluripotent stem cells, or normal cells that are seeded/printed in an abnormal or aberrant configuration.

In one embodiment, a single type of cells is seeded onto a patterned soft substrate. In another embodiment, two or more types of cells are seeded onto a patterned soft substrate to produce, e.g., an island of one cell type surrounded by a second cell type. In some cases, both muscle cells and neuronal cells are present.

To seed cells, patterned soft substrates are placed in culture with a cell suspension allowing the cells to settle and adhere to the patterned soft substrate. In the case of an adhesive surface treatment, cells bind to the material in a manner dictated by the surface chemistry. For patterned chemistry, cells respond to patterning in terms of growth and function. Examples of cell types that are attached include myocytes (e.g., cardiac myocytes) for muscle-based motion; neurons for electrical-signal propagation; fibroblasts for extra-cellular-matrix propagation; endothelial cells for blood contact; smooth muscle cells for slow, tonic contraction; and skin cells. Other cells include stem cells that may differentiate, de-differentiate, change potency or otherwise alter gene expression. The cells on the substrates may be cultured in an incubator under physiologic conditions (e.g., at 37° C.) until the cells form a two-dimensional (2D) tissue (i.e., a layer of cells that is less than 200 microns thick, or, in particular embodiments, less than 100 microns thick, or even just a monolayer of cells), the anisotropy or isotropy of which is determined by the engineered surface chemistry.

In particular embodiments, the extracellular-matrix protein, fibronectin, is used to functionalize a substrate. Cardiomyocytes cultured on different uniform and patterned layers of fibronectin produce 2D myocardium with different microstructures. Uniform fibronectin coatings produce isotropic 2D myocardium with no long-range order. Patterns of alternating high and low density 20-µm-wide fibronectin lines produce continuous anisotropic 2D myocardium. Patterns of alternating 20-µm-wide lines of high-density fibronectin and Pluronics produce a discontinuous array of anisotropic 1D myocardial strips. Patterns of circles, square, rectangular or triangle produce single cardiomyocytes of corresponding shape.

II. Uses of the Soft Substrates of the Invention

The patterned soft substrates produced according to the methods of the invention may be used in various applications e.g., to measure various cellular activities or functions, such as the contractility of cells with engineered shapes and connections, the mechano-electrical coupling of cells, the mechano-chemical coupling of cells, and/or the response of the cells to varying degrees of substrate rigidity.

Cellular activities or functions that can be measured include, e.g., biomechanical forces that result from stimuli that include, but are not limited to, cell contraction, osmotic swelling, structural remodeling and tissue level pre-stress, and electrophysiological responses, in a non-invasive manner, for example, in a manner that avoids cell damage, and in an manner replicating an in vivo environment.

Accordingly, the present invention provides methods for assaying a cellular activity. The methods include providing a patterned soft substrate comprising cells seeded thereon and evaluating a cellular activity of the cells seeded on said patterned soft substrate, such as a biomechanical or electrophysiological activity. The methods may include evaluating a biomechanical or electrophysiological activity at one time point or more than one time point.

For example, using a patterned soft substrate prepared as described herein comprising, e.g., fluorescent beads, the motility of a cell, cell growth, cell spreading, and/or the effect of a stimulus on a cell, can be evaluated by analyzing the displacement of the fluorescent beads, e.g., using traction force analysis.

In one embodiment, such an assay may be used to evaluate the contractility of muscle cells with engineered shape and connection. This assay evaluates the contraction response of a given cell type when exposed to varying stimuli. In another embodiment, such an assay may be used to evaluate the mechanical communication between cells (cell-cell) or between cell and extracellular matrix (cell-matrix). Such an assay could evaluate the relationship between cellular shape, orientation, or distance to the cell-cell or cell-matrix communication. In another embodiment, such an assay may be used to evaluate the mechanics of a cell's nucleus. The effect of varying substrate rigidity on cellular structure and function may also be evaluated using the assays of the invention. Other assays include mechano-electrical or mechano-chemical coupling of cells, varying cell shape and connection.

The assays of the present invention may further comprise, e.g., imaging the cells on the soft substrate and/or staining the cells on the soft substrate for a particular cell type or gene or protein expression.

The patterned soft substrates of the present invention are also useful for investigating tissue developmental biology and disease pathology, as well as in drug discovery and toxicity testing by, e.g., seeding the soft substrates prepared according to the methods of the invention with a cell(s) and culturing the cell(s) such that a bioengineered tissue is formed.

Accordingly, the present invention also provides methods for identifying a compound that modulates a cellular activity. The methods include contacting a patterned soft substrate prepared as described herein and seeded with, e.g., a muscle cell; with a test compound; and determining the effect of the test compound on a cellular activity of the cells seeded on said patterned soft substrate in the presence and absence of the test compound, wherein a modulation of the cellular activity in the presence of said test compound as compared to the cellular activity in the absence of said test compound indicates that said test compound modulates a cellular activity, thereby identifying a compound that modulates a cellular activity.

In another aspect, the present invention provides methods for identifying a compound useful for treating or preventing a disease. The methods include contacting a patterned soft substrate prepared according to the methods of the invention and seeded with cells with a test compound; and determining the effect of the test compound on a cellular activity of the cells seeded on said patterned soft substrate in the presence and absence of the test compound, wherein a modulation of cellular activity in the presence of said test compound as compared to the cellular activity in the absence of said test compound indicates that said test compound modulates a cellular activity, thereby identifying a compound useful for treating or preventing a disease.

The methods of the invention generally comprise determining the effect of a test compound on a plurality of cells or cell types, e.g., a tissue, however, the methods of the invention may comprise further evaluating the effect of a test compound on an individual cell type(s).

The present invention also includes the production of arrays. Arrays of patterned soft substrates prepared according to the methods described herein may be prepared using, for example, multi-well plates or tissue culture dishes so that each cell seeded on a patterned soft substrate in a particular well may be exposed to a different compound to investigate the effect of the compound on the cell (e.g., altered expression of a given protein/cell surface marker, or altered differentiation). Thus, the screening methods of the invention may involve contacting a single cell or tissue with a test compound or a plurality of cells or tissues with a test compound.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a cell or tissue seeded on a patterned soft substrate prepared according to the methods described herein with a test compound) is intended to include any form of interaction (e.g., direct or indirect interaction) of a test compound and a cell or tissue on or within a patterned soft substrate. The term contacting includes incubating a compound and a cell or tissue on or within a patterned soft substrate (e.g., adding the test compound to a cell or tissue).

Test compounds, may be any agents including chemical agents (such as toxins), small molecules, pharmaceuticals, peptides, proteins (such as antibodies, cytokines, enzymes, and the like), and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to a cell or tissue on or within a patterned soft substrate by any suitable means. For example, the test compound may be added drop-wise onto the surface of a cell or tissue on or within a patterned soft substrate and allowed to diffuse into or otherwise enter the cell or tissue, or it can be added to the nutrient medium and allowed to diffuse through the medium. In the embodiment where the cell or tissue on or within a patterned soft substrate is cultured in a multi-well plate, each of the culture wells may be contacted with a different test compound or the same test compound. In one embodiment, the screening platform includes a microfluidics handling system to deliver a test compound and simulate exposure of the microvasculature to drug delivery.

Numerous physiologically relevant parameters, e.g., insulin secretion, conductivity, neurotransmitter release, lipid production, bile secretion, e.g., muscle activities, e.g., biomechanical and electrophysiological activities, can be evaluated in the methods of the invention. For example, in one embodiment, cells seeded onto the soft substrates of the present invention can be used in contractility assays for muscular cells or tissues, such as chemically and/or electrically stimulated contraction of vascular, airway or gut smooth muscle, cardiac muscle or skeletal muscle. In addition, the differential contractility of different muscle cell types to the same stimulus (e.g., pharmacological and/or electrical) can be studied.

In another embodiment, cells seeded onto the patterned soft substrates of the present invention can be used for measurements of solid stress due to osmotic swelling of cells. For example, as the cells swell the soft substrate will deform and as a result, volume changes, force and points of rupture due to cell swelling can be measured.

In another embodiment, cells seeded onto the soft substrates of the present invention can be used for pre-stress or residual stress measurements in cells. For example, vascular smooth muscle cell remodeling due to long term contraction in the presence of endothelin-1 can be studied.

Further still, cells seeded onto the patterned soft substrates of the present invention can be used to study the loss of rigidity in tissue structure after traumatic injury, e.g., traumatic brain injury. Traumatic stress can be applied to vascular smooth muscle bioengineered tissues as a model of vasospasm. These bioengineered tissues can be used to determine what forces are necessary to cause vascular smooth muscle to enter a hyper-contracted state. These bioengineered tissues can also be used to test drugs suitable for minimizing vasospasm response or improving post-injury response and returning vascular smooth muscle contractility to normal levels more rapidly.

In other embodiments, cells seeded onto the patterned soft substrates of the present invention can be used to study biomechanical responses to paracrine released factors (e.g., vascular smooth muscle dilation due to release of nitric oxide from vascular endothelial cells, or cardiac myocyte dilation due to release of nitric oxide).

In other embodiments, cells seeded onto the patterned soft substrates of the invention can be used to evaluate the effects of a test compound on an electrophysiological parameter, e.g., an electrophysiological profile comprising a voltage parameter selected from the group consisting of action potential, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release. For example, a decrease in a voltage or calcium flux parameter of a bioengineered tissue comprising cardiomyocytes upon contacting the bioengineered tissue with a test compound, would be an indication that the test compound is cardiotoxic.

In yet another embodiment, cells seeded onto the patterned soft substrates of the present invention can be used in pharmacological assays for measuring the effect of a test compound on the stress state of a tissue. For example, the assays may involve determining the effect of a drug on tissue stress and structural remodeling of bioengineered tissues. In addition, the assays may involve determining the effect of a drug on cytoskeletal structure and, thus, the contractility of the bioengineered tissues.

In still other embodiments, cells seeded onto the patterned soft substrates of the present invention can be used to measure the influence of biomaterials on a biomechanical response. For example, differential contraction of vascular smooth muscle remodeling due to variation in material properties (e.g., stiffness, surface topography, surface chemistry or geometric patterning) of bioengineered tissues can be studied.

In further embodiments, cells seeded onto the patterned soft substrates of the present invention can be used to study functional differentiation of stem cells (e.g., pluripotent stem cells, multipotent stem cells, induced pluripotent stem cells, and progenitor cells of embryonic, fetal, neonatal, juvenile and adult origin) into contractile phenotypes. For example, undifferentiated cells are seeded onto the soft substrates of the invention, e.g., stem cells, and differentiation into a contractile phenotype is observed by evaluating soft substrate displacement. Differentiation can be observed as a function of: co-culture (e.g., co-culture with differentiated cells), paracrine signaling, pharmacology, electrical stimulation, magnetic stimulation, thermal fluctuation, transfection with specific genes and biomechanical perturbation (e.g., cyclic and/or static strains)

In another embodiment, cells seeded onto the patterned soft substrates of the invention may be used to determine the toxicity of a test compound by evaluating, e.g., the effect of the compound on an electrophysiological response of a bioengineered tissue. For example, opening of calcium channels results in influx of calcium ions into the cell, which plays an important role in excitation-contraction coupling in cardiac and skeletal muscle fibers. The reversal potential for calcium is positive, so calcium current is almost always inward, resulting in an action potential plateau in many excitable cells. These channels are the target of therapeutic intervention, e.g., calcium channel blocker sub-type of anti-hypertensive drugs. Candidate drugs may be tested in the electrophysiological characterization assays described herein to identify those compounds that may potentially cause adverse clinical effects, e.g., unacceptable changes in cardiac excitation, that may lead to arrhythmia.

For example, unacceptable changes in cardiac excitation that may lead to arrhythmia include, e.g., blockage of ion channel requisite for normal action potential conduction, e.g., a drug that blocks $Na^+$ channel would block the action potential and no upstroke would be visible; a drug that blocks $Ca^{2+}$ channels would prolong repolarization and increase the refractory period; blockage of $K^+$ channels would block rapid repolarization, and, thus, would be dominated by slower $Ca^{2+}$ channel mediated repolarization.

In addition, metabolic changes may be assessed to determine whether a test compound is toxic by determining, e.g., whether contacting a bioengineered tissue with a test compound results in a decrease in metabolic activity and/or cell death. For example, detection of metabolic changes may be measured using a variety of detectable label systems such as fluormetric/chromogenic detection or detection of bioluminescence using, e.g., AlamarBlue fluorescent/chromogenic determination of REDOX activity (Invitrogen), REDOX indicator changes from oxidized (non-fluorescent, blue) state to reduced state (fluorescent, red) in metabolically active cells; Vybrant MTT chromogenic determination of metabolic activity (Invitrogen), water soluble MTT reduced to insoluble formazan in metabolically active cells; and Cyquant NF fluorescent measurement of cellular DNA content (Invitrogen), fluorescent DNA dye enters cell with assistance from permeation agent and binds nuclear chromatin. For bioluminescent assays, the following exemplary reagents is used: Cell-Titer Glo luciferase-based ATP measurement (Promega), a thermally stable firefly luciferase glows in the presence of soluble ATP released from metabolically active cells.

Cells seeded onto the patterned soft substrates of the invention are also useful for evaluating the effects of particular delivery vehicles for therapeutic agents e.g., to compare the effects of the same agent administered via different delivery systems, or simply to assess whether a delivery vehicle itself (e.g., a viral vector or a liposome) is capable of affecting the biological activity of the bioengineered tissue. These delivery vehicles may be of any form, from conventional pharmaceutical formulations, to gene delivery vehicles. For example, cells seeded onto the soft substrates of the invention may be used to compare the therapeutic effect of the same agent administered by two or more different delivery systems (e.g., a depot formulation and a controlled release formulation). Cells seeded onto the patterned soft substrates of the invention may also be used to investigate whether a particular vehicle may have effects of itself on the tissue. As the use of gene-based therapeutics increases, the safety issues associated with the various possible delivery systems become increasingly important. Thus, the bioengineered tissues of the present invention may be used to investigate the properties of delivery systems for nucleic acid therapeutics, such as naked DNA or RNA, viral vectors (e.g., retroviral or adenoviral vectors), liposomes and the like. Thus, the test compound may be a delivery vehicle of any appropriate type with or without any associated therapeutic agent.

Furthermore, cells seeded onto the patterned soft substrates of the present invention are a suitable in vitro model for evaluation of test compounds for therapeutic activity with respect to, e.g., a muscular and/or neuromuscular disease or disorder. For example, the bioengineered tissues of the present invention (e.g., comprising muscle cells) may be contacted with a candidate compound by, e.g., immersion in a bath of media containing the test compound, and the effect of the test compound on a tissue activity (e.g., a biomechanical and/or electrophysiological activity) may measured as described herein, as compared to an appropriate control, e.g., an untreated bioengineered tissue. Alternatively, a bioengineered tissue of the invention may be bathed in a medium containing a candidate compound, and then the cells are washed, prior to measuring a tissue activity (e.g., a biomechanical and/or electrophysiological activity) as described herein. Any alteration to an activity determined using the bioengineered tissue in the presence of the test agent (as compared to the same activity using the device in the absence of the test compound) is an indication that the test compound may be useful for treating or preventing a tissue disease, e.g., a neuromuscular disease.

This invention is further illustrated by the following examples which should not be construed as limiting. The contents of all references, patents and published patent applications cited throughout this application, as well as the Figures, are hereby incorporated by reference.

EXAMPLES

The following materials and methods were used throughout the Examples:

Cardiac Myocyte Culture

Trypsinized ventricular tissue isolated from 2-day old neonatal Sprague Dawley rats (Charles River Laboratories, Wilmington, Mass.) was serially dissociated into single cells by treating the ventricular tissue 4 times with a 0.1% solution of collagenase type II (Worthington Biochemical, Lakewood, N.J.) for 2 minutes at 37° C. The myocyte fraction was purified and pre-plating the cells twice for 45 minutes each time. Purified myocytes were plated onto patterned substrates prepared as described below at a density of 100,000 cells per coverslip and kept in culture at 37° C. with a 5% CO atmosphere. The culture medium was M199 (Invitrogen, Carlsbad, Calif.) base supplemented with 10% heat-inactivated Fetal Bovine Serum, 10 mM HEPES, 20 mM glucose, 2 mM L-glutamine, 1.5 vitamin B-12, and 50 U/mi penicillin. The medium was changed 24 hours after plating to remove unattached and dead cells and every 48 hours afterwards. After 72 hours in culture, most cardiac myocytes beat spontaneously and were used either for immunostaining or traction force measurements.

Patterning Substrates

Patterned substrates containing square, triangular, or circular adhesive islands were prepared for immunostaining and traction force microscopy, as follows. Briefly, a thin layer of 10% by weight poly-N-iso-propylacrylamide (PIPAAM) prepared in 1-butanol was spin coated on a silicon wafer (FIG. 3a). A 50-75 µm layer of photoresist (SU-8, MichroChem Corp, Newton, Mass.) was spin-coated on top of the PIPAAM (FIG. 3b), UV light treated through a photolithographic mask (FIG. 3c), and developed to obtain a complementary master that contained holes with the same size and shape as the desired adhesive islands (FIG. 3d). The master was immersed in ice water to dissolve the PIPAAM and the photoresist membrane was released from the wafer (FIG. 3e). Polyacrylamide gels (0.1% bis and 5% acrylamide; about 90 µm thick) containing 1:500 volume of carboxylate-modified fluorescence latex beads (about 0.2 µm Fluospheres, Molecular Probes, Eugene, Oreg.) were fabricated on 25 mm coverslips.

The Young's modulus of the gel was estimated to be about 3 KPa using atomic force microscopy. The photoresist membrane was placed on the surface of the gel and 1 mM sulfo-SANPAH (sulfosuccinimidyl-6-4-azido-2-nitrophenylamino-hexanoate; Pierce, Rockford, Ill.) in 50 mM HEPES was added through the holes in the photoresist membrane. The whole system was then placed under vacuum for 3 minutes to ensure that the sulfo-SANPAH reached the gel surface.

The surface of the gel that contacted with the sulfo-SANPAH was photoactivated by UV light exposure (FIG. 3f). After excess sulfo-SANPAH was removed, fibronectin (FN) 100 µg/mL was added to the membrane and the gel was placed under vacuum for another 3 minutes to remove bubbles from the holes (FIG. 3g). The FN was allowed to react with the photoactivated gel for at least 4 hours at 37° C. to create FN-coated adhesive islands. Excess FN was washed away with PBS. After removal of the photoresist membrane, the gel was immediately used for cell plating (FIG. 3h).

Traction Force Microscopy Data Measurement and Analysis

Coverslips containing the beating myocytes were removed from the incubator, mounted onto a custom-made microscope stage containing a bath chamber, and continuously perfused with 37° C. normal Tyrode's solution (1.192 g of HEPES, 0.901 g of glucose, 0.265 g of CaCh, 0.203 g of MgCb, 0.403 g of KCl, 7.889 g of NaCl and 0.040 g of NaH2PO4 per liter of deionized water, reagents from Sigma, St. Louis, Mo.). Fluorescence images of gels containing fluorescent beads immediately beneath the contracting myocytes were taken at 28.1 Hz. The duration of image acquisition was long enough to include at least two complete cycles of contraction-relaxation of individual myocytes. Consecutive images were paired and the prior image was used as a reference to measure the change of the position of the fluorescence beads using the algorithm described previously (Butler et al., *Am. J. Physiol. Cell Physiol.*, 2002, 282:C595-605). This yielded the discretized displacement field between two consecutive frames. The calculated displacements were summed up for a whole systolic cycle to determine the overall 2D displacement field. The systolic traction field was calculated from the displacement field by adapting the algorithm previously developed (Dembo and Wang, *Biophys. J.*, 1999, 76:2307-23 16 and Schwarz et al., *Biophys. J.*, 2002, 83:1380-1394). This algorithm solved the inverse of the Boussinesq solution from the displacement field on the surface of an elastic halfspace to obtain the traction field when the mechanical properties of the gel are known.

The Poisson ratio of the gel was assumed to be close to 0.5. The interior of the cell was subdivided into 4×4 µm² squares to approximate the discretized localization of contractile forces. The ability of a particular solved traction field to explain the observed displacements was estimated with $X^2$ statistics. In addition to a zero-order Tikhonov regularization, a constraint that the forces should not become exceedingly large was used to minimize and stabilize the solution. The L-curve criterion (Schwarz et al., Biophys. J., 2002, 83:1380-1394) was used to determine the optimal balance between the data agreement and the regularization.

Immunofluorescent Staining and Imaging

Cardiac myocytes stained for actin (Alexa 488 Phalloidin, Molecular Probes), vinculin (clone hVIN-1, Sigma), and sarcomeric α-actinin (clone EA-53, Sigma) were fixed in 4% PFA with 0.01% Triton X-100 in PBS buffer at 37° C. for 15 minutes and equilibrated to room temperature during incubation. Secondary staining was performed using tetramethylrhodamine conjugated goat anti-mouse IgU (Alexa Fluor 594, Molecular Probes), and nuclei were visualized by staining with 4',6'-diamidino-2-phenylindole hydrochloride (DAPI, Molecular Probes). All fluorescence and traction force microscopy was conducted with a Leica DM1 6000B microscope, using a 63× plan-apochromat objective. For traction force experiments, images were collected with a Cascade 512b enhanced CCD camera, while immunofluorescence images were collected with a CoolSnap J4Q CCD camera (both from Roper Scientific, Tucson, Ariz.) controlled by IPLab Spectrum (BD Biosciences/Scanalytics, Rockville, Md.).

Example 1

Self-Assembly and Organization of Muscle Cells

It was hypothesized that the spatial arrangement of mature myofibrils can be achieved in principle via two temporally ordered, mutually interacting mechanisms. The first mechanism, occurring on the scale of seconds to minutes, involves stress fiber synthesis and formation of their anchoring focal adhesions (FAs), and provides a structural basis for premyofibril assembly. This mechanism is sensitive to spatial cues imposed on cellular boundary conditions and is herein referred to as the extrinsic process. The second mechanism is a slower intrinsic process, where adjacent premyofibrils preferentially align in parallel over a time scale of hours. It is proposed here that the temporal differences between the extrinsic and intrinsic mechanisms establish a hierarchy amongst these processes that govern the organization of the contractile cytoskeleton.

To test this hypothesis, a theoretical model was developed that broadens the spatial scale to the whole cell and temporally focusing on the steps preceding sarcomere assembly. This theoretical model semi-quantitatively recapitulates FA assembly and the cytoplasmic arrangement and bundling of myofibrils in 2D myocytes. For simplicity, six field variables were focused upon, most of which can be observed To verify the computational results, culture substrates were used containing micrometer-sized extracellular matrix (ECM) islands fabricated by microcontact printing to analyze the effects of ECM-dependent changes in cell shape on myofibrillar patterning. When freshly harvested neonatal rat ventricular myocytes are cultured on individual islands surrounded by nonadhesive regions, the myocytes remodel to take on the shape of the islands. These simulation data show that well-aligned premyofibrils first occurred in the earliest time point in the center of the cell, followed the longest diagonal, and recruited additional adjacent fibers to form a bundled, parallel arrangement. This is consistent with the fluorescent staining against actin filaments of myocytes cultured on similarly shaped islands for three days that this model accurately predicts the spatial organization of myofibrils with respect to complex cues in the ECM.

To test this hypothesis further, the sensitivity of myocytes and this model to various cellular boundary conditions were examined. It was reasoned that myocytes patterned on islands of heterogeneous boundary curvature have both extrinsic and intrinsic processes that potentiate the organization of the cytoskeletal network. But when cells are cultured on islands of homogeneous boundary curvature, there is no external cue to break the symmetry of the isotropic cytoskeleton and thus the cells are dependant on slower, intrinsic events to polarize the myofibrillar array. Thus, two cases of the cell with heterogeneous curvature at the periphery were examined: the square shaped cell, where the longest axes are on the diagonal and the equilateral triangle shaped cell, where the long axes are along the cell periphery. One example of cells with homogeneous boundary curvature was also tested: the circular shaped cell, in which no long axis is preferentially defined. To ensure that the observations resulted from geometric considerations alone, the same parameter values were applied across the different shapes in all simulations.

Figure 1:
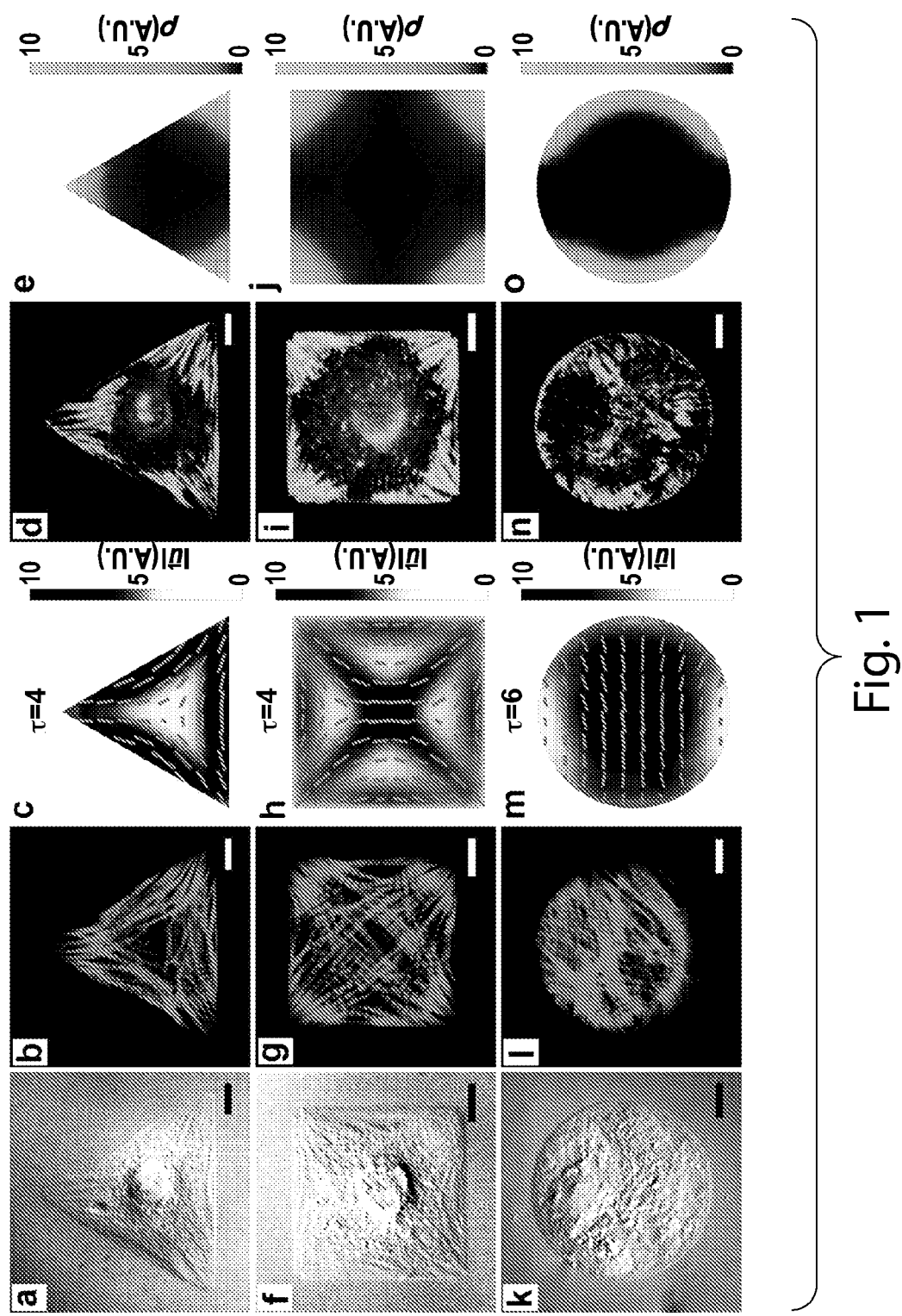
FIG. 1 depicts experimental images and model depictions of organization of actin and focal adhesions (FA). First column: DIC images of patterned triangular (a), square (f), and circular (k) myocytes. Second column: Immunostained actin in triangular (b) and square (g) myocytes followed the longest cellular dimension, while actin fibers in the circular myocyte (l) primarily oriented on the 2 to 8 o'clock axis. Third column: Predicted premyofibrillar pattern of triangular (c), square (h), and circular (m) myocytes agrees with experimental results. The steady state of the circular cell occurred slower than that of the triangular and square cells. The grayscale and lines represent premyofibril bundling and local orientation, respectively. Fourth column: Immunostained vinculin of triangular (d) and square (i) myocytes was concentrated at cellular corners, while two opposing plaques of vinculin localized on the 2 to 8 o'clock axis in the circular (n) myocyte. Fifth column: Simulated FA density at steady state in triangular (e), square (j), and circular (o) cells was consistent with experimental results. The FA distribution in a circular myocyte (o) was expected to break the symmetry. Grayscale values in simulated results are in arbitrary units; scale bars are 10 μm.

Fluorescent staining of actin filaments in myocytes cultured on square and triangular ECM islands revealed that polymerized actin fibers were densely arranged along the longest axes (FIG. 1). The fibers are regularly punctuated along their length, highlighting the presence of sarcomeres (FIG. 1b, g). At steady state, modeled triangular and square cells displayed the same cytoskeletal arrangement as the in vitro results, with enhanced parallel bundling occurring along the longest axis of these cells (FIG. 1c, h). Fluorescent staining of vinculin in the same myocytes revealed elongated FAs in the corners of the square and triangular cells that were oriented in parallel with their attached myofibrils (FIG. 1d, i). Numerical results revealed the same accumulation pattern of FAs, as indicated by the density of bound integrand located in the corners (FIG. 1e, j). As indicated in the figure and previously observed in the simulation, these architectures appeared after four epochs of the simulation, with the predominant orientation of the premyofibrils occurring quickly and the parallel bundling increasing with time to further stabilize the myofibrillar architecture with respect to the geometric cues in the ECM.

These data suggest that FAs localize and mature at the corners because the stress fibers and premyofibrils that align along the longest axes of the cell are the strongest by virtue of their greater propensity for parallel bundling and binding myosin motors.

Figure 2:
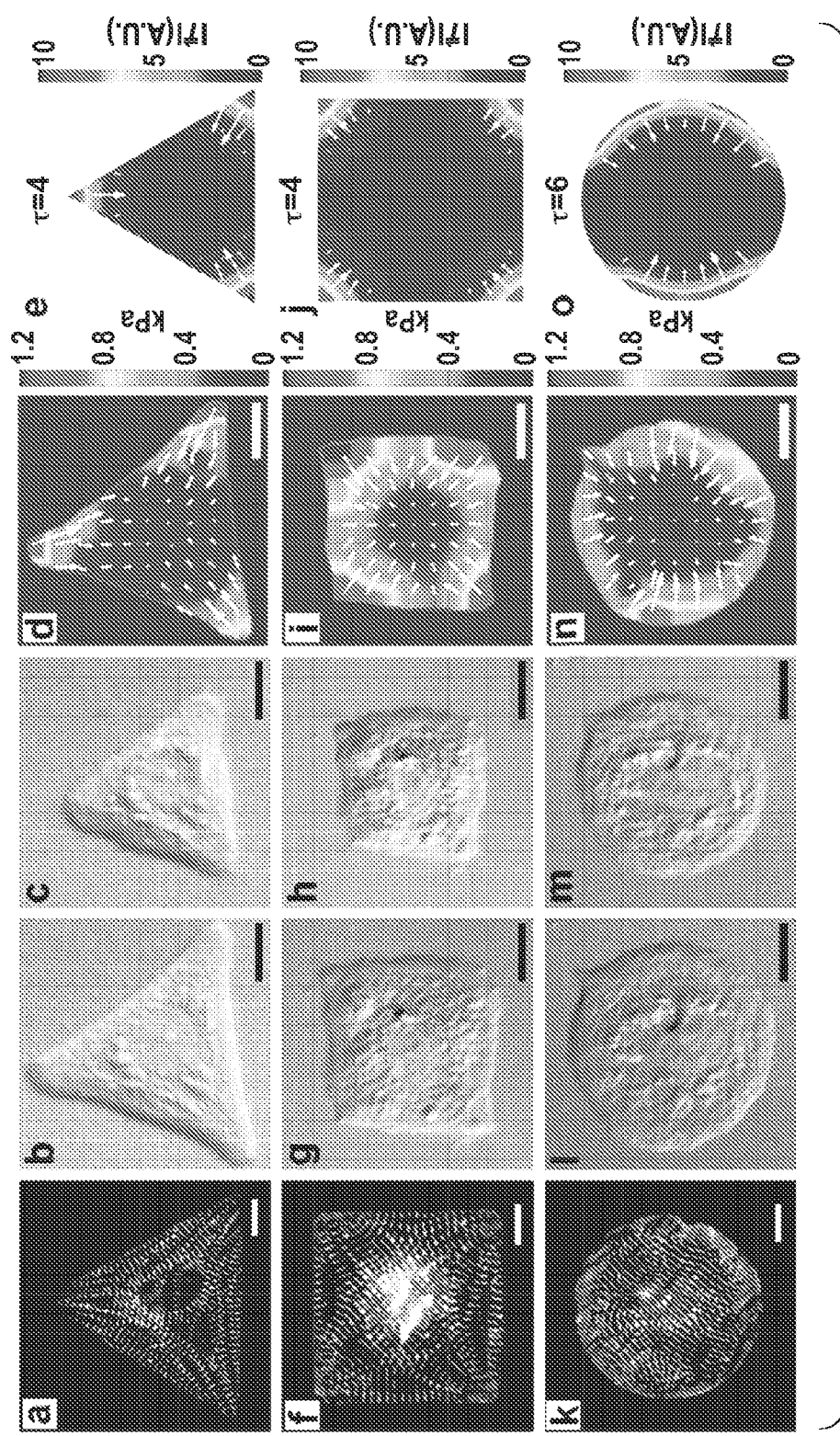
FIG. 2 depicts sarcomeric structure, traction force at peak systole, and model predictions. First column: Sarcomeric a-actinin immunofluorescence delineates the Z-lines in triangular (a), square (l) and circular (k) myocytes. Z-line orientation indicated that the axis of contraction was parallel to the longest axis of the cell. In the circular myocyte, most of the Z-lines aligned on the 1 to 7 o'clock axis with the dominant axis of contraction expected to follow the 4 to 10 o'clock direction. Second column: DIC images of patterned triangular (b), square (g), and circular (l) myocytes at full relaxation. Third column: DIC images at full contraction of the triangular (c), square (h), and circular (m) myocytes show the cells shortened about 24%, 18%, and 14% along the longest cell dimension, respectively. Fourth column: The contractile traction map of the triangular (d) and square (i) myocytes displayed high fractions at the cellular corners. The contraction map of the circular myocyte (n) indicated that the cell broke radial symmetry, with the principal axis of contraction along the 3 to 9 o'clock axis. Fifth column: Numerical results of predicted traction map of triangular (e), square (j), and circular (o) myocytes replicated experimental results. In the fourth and fifth columns, the grayscale and arrows represent the magnitude and direction of traction, respectively. Grayscale values in simulated results are in arbitrary units; scale bars are 10 μm.

In contrast, actin-stained myocytes cultured on circular ECM islands (FIG. 1k) for the same period of time as the square and triangular myocytes polarized their cytoskeleton but not along a repeatable axis (FIG. 1l). As hypothesized, without an external cue to break the symmetry of the self-organizational processes, computer simulations suggest that myofibrillar polarity will emerge after six epochs through the slow, intrinsic process. Transient multi-pole patterns develop prior to equilibrium where the cytoskeleton is anisotropic, with parallel bundles of polymerized microfilaments extending across the diameter of the cell (FIG. 1m). In vitro, vinculin stains irregularly around the myocyte perimeter (FIG. 1n). In silico, after a similarly prolonged simulation, FAs appear as opposing bands along the cell periphery (FIG. 1o). It is important to note that this patterning is due to a random, intercellular, symmetry-breaking event and that while the model will always converge on a polarized cell with anisotropic cytoskeletal architecture, circular cells in vitro often display irrepeatable cytoskeletal structures after 2-3 days in culture. Together, the simulation and experimental results summarized in FIG. 1 suggested that the faster extrinsic process of stress fiber alignment is regulated by ECM cues. These cues promote stabilization of the stress fibers and FAs long enough for parallel bundling of the premyofibrils and myofibrillogenesis to occur. Furthermore, this model predicted that the polarized myofibrillar network has a preference to align along the longest axis of cells, consistent with a previous report that the stress fiber length is comparable to the cell size. Proper functioning of myocytes requires the correct myofibrillar configuration for coordinated contraction. To correlate myofibrillar patterning with contractile function, the spatial patterning of sarcomeric proteins was investigated and traction force microscopy on the cultured myocytes was conducted. Fluorescent micrographs of myocytes immunostained against sarcomeric a-actinin revealed distinct myofibrillar patterning on ECM islands of heterogeneous curvature (FIG. 2a, f). The sarcomeric Z-lines register in the internal angles of the corners of both the square and triangle and are perpendicular to the orientation of the actin fibers. To measure myocyte contractile stresses, ECM islands on soft substrates were engineered. When freshly harvested myocytes are cultured on these substrates, they remodel to assume the shape of the island in the same manner as they do on rigid substrates (FIG. 2b, g). Unlike myocytes cultured on the rigid substrates, myocytes on soft substrates do not contract isometrically and can be observed to shorten as in traditional assays of single myocyte contractility (FIG. 2c, h). To visualize substrate deformation due to myocyte contraction, fluorescent beads were embedded in the substrate and bead movement was detected using high speed fluorescence microscopy. The nominal stress field exerted on the substrate due to systolic contraction, with the resting myocyte position defined as the reference state, was calculated from substrate deformation with the known substrate mechanical properties and the assumption of substrate linear elasticity. The substrate displacement vectors, as depicted by the white arrows, are directed inward during systole, indicating that the substrate is pulled towards the center of the myocyte by the shortening FA-anchored myofibrils. During diastole, they reversed direction as the elastic recoil of the myocyte pushed the substrate back to the rest position. The myocytes generate a unique contractile footprint that mimics the position of the FAs depicted in FIG. 1, with the highest systolic stresses exerted on the substrate at the corners of the myocyte (FIG. 2d, i). Note that even though the model does not differentiate between systolic and diastolic stresses, the experimental substrate stress field pattern matches the simulated results (FIG. 2e, j).

In myocytes of homogeneous boundary curvature, sarcomere patterns are not reproducible. However, structural coordination of the myofibrils on a preferential axis was observed, as evidenced by the well-demarcated Z-lines that continuously traversed the 1 to 7 o'clock axis in the circular myocyte shown in FIG. 2k. Similarly, the circular shaped myocytes cultured on soft substrates appear to shorten concentrically during contraction (FIG. 2l, m), with that a principal axis of shortening is apparent at full contraction but does not occur with the same spatial regularity of the square and triangular cells (FIG. 2n), consistent with previous findings with non-muscle cells. This model predicted a similar contractile signature (FIG. 2o), with the peak stresses coincident with the location of the widest FA bands observed in FIG. 1o. Overall, the data in FIG. 2 demonstrate that the functional implication of myofibril organization is to maximize the contractility of myofibrillar bundles by arranging them to span the greatest distance possible within the cell and be well-aligned with adjacent bundles.

Thus, for a cardiac muscle cell to properly align its myofibrils in the most efficient manner, a local symmetry break is required to potentiate the assembly and organization of the actin network template. Such cytoskeletal symmetry-breaking has also been widely observed in other important biological behaviors such as cellular migration, cellular division, and formation of tissue sheets. The symmetry-breaking can arise from a static, external cue, such as a geometric feature in the boundary conditions imposed on the cell, or from a dynamic internal cue, such as a locally increased fiber density. The multiple time scales of these interacting events suggest a hierarchy of post-translational, self-organizational processes that are required for coupling cellular form and function.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by 1/20th, 1/10th, 1/5th, 1/3rd, 1/2, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed is:

1. A method for generating a patterned soft substrate, the method comprising
    providing a base layer;
    depositing a sacrificial polymer on the base layer, thereby generating a sacrificial polymer layer;
    depositing a photoresist onto the sacrificial polymer layer, thereby generating a photoresist layer;
    placing a mask comprising a pattern on top of the photoresist layer and exposing the photoresist layer to electromagnetic radiation, thereby generating a patterned photoresist complementary mask comprising the complement of the pattern of the mask;
    releasing the patterned photoresist complementary mask from the sacrificial polymer layer;
    placing the patterned photoresist complementary mask onto a soft substrate such that the patterned photoresist complementary mask makes conformal contact with the soft substrate; and
    functionalizing the portion of the soft substrate that is exposed by the pattern in the patterned photoresist complementary mask by depositing a linker molecule and a biopolymer onto the soft substrate, wherein the linker molecule associates with the biopolymer and the soft substrate to attach the biopolymer to the portion of the soft substrate exposed by the pattern;
    thereby generating the patterned soft substrate.

2. The method of claim 1, further comprising seeding cells on said patterned soft substrate.

3. The method of claim 1, wherein the base layer is a silicon wafer.

4. The method of claim 1, wherein the biopolymer is fibronectin.

5. The method of claim 1, wherein the linker molecule is a bifunctional or multifunctional linker molecule.

6. The method of claim 1, wherein the linker molecule is N-Sulfosuccinimidyl 6-hexanoate (SANPAH).

7. The method of claim 1, wherein the soft substrate has a Young's modulus of about 1 to about 100,000 pascal (Pa).

8. The method of claim 1, wherein the photoresist is an epoxy-novolac resin.

9. The method of claim 1, wherein the patterned photoresist complementary mask is removed prior to depositing the biopolymer.

10. The method of claim 1, wherein the patterned photoresist complementary mask is not removed prior to depositing the biopolymer.

11. The method of claim 2, wherein said cells are muscle cells.

12. The method of claim 11, wherein said muscle cells are cardiomyocytes.

13. The method of claim 11, wherein said cells are vascular smooth muscle cells.

14. The method of claim 1, wherein the biopolymer is selected from the group consisting of an extracellular matrix protein, a growth factor, a lipid, a fatty acid, a steroid, a sugar, a carbohydrate, a proteoglycan, a glycoprotein, a glycolipid, a biologically derived homopolymer, a nucleic acid molecule, a hormone, an enzyme, a pharmaceutical, a cell surface ligand, a cell surface receptor, a cytoskeletal filament, and a cytoskeletal motor protein.

15. The method of claim 1, wherein the soft substrate comprises fluorescent beads.

16. A method for generating a patterned soft substrate, the method comprising
    providing a base layer;
    depositing a sacrificial polymer on the base layer, thereby generating a sacrificial polymer layer;
    depositing a photoresist onto the sacrificial polymer layer, thereby generating a photoresist layer;
    placing a mask comprising a pattern on top of the photoresist layer and exposing the photoresist layer to electromagnetic radiation, thereby generating a patterned photoresist complementary mask comprising a pattern that is the complement of the pattern in the mask;
    releasing the patterned photoresist complementary mask from the sacrificial polymer layer;
    placing the patterned photoresist complementary mask onto a soft substrate such that the patterned photoresist complementary mask makes conformal contact with the soft substrate; and
    functionalizing the portion of the soft substrate that is exposed by the pattern in the patterned photoresist complementary mask by depositing a repellant onto the soft substrate;
    removing the patterned photoresist complementary mask; and
    depositing a linker molecule and a biopolymer onto the soft substrate, wherein the linker molecule associates with the biopolymer and the soft substrate to attach the biopolymer to the portion of the soft substrate on which repellant was not deposited;
    thereby generating the patterned soft substrate.

* * * * *